(12) United States Patent
Besselink et al.

(10) Patent No.: US 7,794,416 B2
(45) Date of Patent: Sep. 14, 2010

(54) ORTHOSIS WITH MULTIPLE HINGES

(75) Inventors: Mark Stefan Besselink, Enschede (NL); Nicolaas Gerardus Adrianus Van Leerdam, Hengelo (NL); Jurrie Van Der Woude, Almelo (NL)

(73) Assignee: Kunst & Van Leerdam IP B.V., Enschede (NL)

( * ) Notice: Subject to any disclaimer, the term of this patent is extended or adjusted under 35 U.S.C. 154(b) by 508 days.

(21) Appl. No.: 10/516,796

(22) PCT Filed: Jun. 5, 2003

(86) PCT No.: PCT/NL03/00418

§ 371 (c)(1),
(2), (4) Date: Aug. 12, 2005

(87) PCT Pub. No.: WO03/103547

PCT Pub. Date: Dec. 18, 2003

(65) Prior Publication Data

US 2006/0100559 A1    May 11, 2006

(30) Foreign Application Priority Data

Jun. 6, 2002   (NL) ................................. 1020777

(51) Int. Cl.
*E05D 3/10*       (2006.01)
*A61B 19/00*      (2006.01)
*A61F 5/37*       (2006.01)
*A61F 5/00*       (2006.01)

(52) U.S. Cl. .............................. 602/16; 602/5; 602/23; 602/26; 128/869; 128/882; 16/367

(58) Field of Classification Search ............... 602/5, 602/16, 18–20, 23–24, 26–27; 128/869, 128/882; 16/367
See application file for complete search history.

(56) References Cited

U.S. PATENT DOCUMENTS

| | | | |
|---|---|---|---|
| 5,421,810 A | 6/1995 | Davis | |
| 5,792,086 A | 8/1998 | Bleau et al. | |
| 5,792,087 A * | 8/1998 | Pringle | 602/27 |
| 5,860,943 A * | 1/1999 | Bloedau et al. | 602/16 |
| 6,027,466 A | 2/2000 | Diefenbacher et al. | |
| 6,036,665 A * | 3/2000 | Towsley | 602/23 |
| 6,090,057 A | 7/2000 | Collins et al. | |
| 6,203,511 B1 | 3/2001 | Johnson et al. | |
| 6,254,559 B1 * | 7/2001 | Tyrrell | 602/16 |

(Continued)

FOREIGN PATENT DOCUMENTS

DE    195 25 671    1/1997

(Continued)

*Primary Examiner*—Patricia M Bianco
*Assistant Examiner*—Brandon Jackson
(74) *Attorney, Agent, or Firm*—The Webb Law Firm

(57) ABSTRACT

An orthopedic device has a structure with two substantially rigid parts, for instance, rods, which rods are coupled to each other by a hinge apparatus and each rod attaches to a fastener for optional temporary fastening to a limb part, wherein a pivot axis of the hinge apparatus extends in the region and in the direction of the pivot axis zone of the relevant joint. The device has an upper hinge and a lower hinge with pivot axes. The respective pivot axes of which extend in directions which make an angle with each other of 90°±40°.

7 Claims, 5 Drawing Sheets

U.S. PATENT DOCUMENTS

| | | | |
|---|---|---|---|
| 6,361,513 B1 * | 3/2002 | Rossi et al. | 602/16 |
| 6,488,644 B1 * | 12/2002 | Ostrom et al. | 602/16 |
| 6,494,853 B1 * | 12/2002 | Rossi et al. | 602/16 |
| 6,656,144 B1 * | 12/2003 | Coligado | 602/16 |
| 7,087,031 B2 * | 8/2006 | Rossi et al. | 602/16 |
| 7,192,408 B2 * | 3/2007 | Win | 602/16 |
| 2002/0133108 A1 * | 9/2002 | Jagodzinski | 602/16 |
| 2003/0229301 A1 * | 12/2003 | Coligado | 602/16 |

FOREIGN PATENT DOCUMENTS

GB     2099309     12/1982

* cited by examiner

ORTHOSIS WITH MULTIPLE HINGES

BACKGROUND OF THE INVENTION

The invention relates to an orthopaedic device, in particular a prosthesis or an orthosis, for the purpose of replacing respectively supporting the function of at least one part of a human limb with a pivotable joint, for example a leg with a knee or an arm with an elbow, on either side of which joint there extend respective limb parts, such as a lower leg and an upper leg respectively a lower arm and an upper arm, which device comprises:

a structure comprising two substantially rigid parts, for instance a rod, which parts are coupled to each other by means of hinge means and each comprise fastening means for optional temporary fastening to a limb part, wherein a pivot axis of the hinge means extends at least more or less in the region and in the direction of the pivot axis zone of the relevant joint.

Such a device is known from for instance U.S. Pat. No. 5,792,086 and GB-A 2 099 309.

SUMMARY OF THE INVENTION

An orthosis is an assist means for supporting a limb with a reduced functionality and can be applied for instance with a paralysed leg. An orthosis consists generally of at least two parts. First of all there are components which stabilize a body joint such as an elbow or an ankle in one or more directions. Such a hinge part generally has one fixed pivot axis.

A first problem of known orthoses is that the construction of an orthosis generally takes place on the basis of a positive plaster model of the shape of the limb in a resting and non-loaded position. Owing to load and to movement the shape of the limb changes, for instance the angle between lower leg and upper leg in the frontal plane. It is the object to mimic the loaded position by manipulating the plaster model, whereafter the construction of the orthosis takes place on the basis of this thus manipulated plaster model. The results of such a manipulation are however not readily predictable, which results in the orthosis having to be corrected afterward, which is difficult and labour-intensive. For this reason the correction is not carried out in some cases, which results in a non-optimal orthosis for the user. A second problem of known orthoses is that a rotation is generally only possible about one fixed main rotation axis of the orthosis which generally corresponds with the characteristic rotation axis of the joint for stabilizing. The characteristic rotation axis makes possible the characteristic movement of a limb, for instance flexing of a knee. In the case of a non-impeded bending of a limb however, the rotation axis of the relevant joint will generally also change direction. This known problem is addressed in the above stated two publications. An orthosis with a fixed main rotation axis therefore obstructs the movement of the relevant joint and the associated limb parts. This obstruction results in undesirable stresses on the joint and the limb parts.

With a view to the above, the invention provides an orthopaedic device of the type stated in the preamble which has the feature that the hinge means comprise two hinges, the respective pivot axes of which extend in directions which make an angle with each other of 90±40, preferably 90±20.

The pivot axes can intersect in the manner of a cardan joint. In a preferred embodiment however, the device according to the invention has the feature that the pivot axes are located spatially at a mutual distance, which distance is chosen such that it corresponds with the pivoting characteristics of the relevant joint. The best possible match can hereby be realized with the pivoting characteristics of the relevant joint.

A preferred embodiment of the device according to the invention is characterized by bounding means for limiting to a chosen angular position at least one of the pivoting movements of at least one of the hinges.

Owing to the stated measures the loaded position can be reached by relative rotation of the orthosis parts without manipulation of the plaster model as discussed above, while the definitive position can be determined during use of the orthosis by adjusting the desired angle with the bounding means adapted for this purpose, whereby a result that is optimal for the user can be achieved in simple manner, without the later correction required in the known orthosis.

A second advantage of the measures according to the invention is that the rotation of the orthosis according to the invention corresponds better to the natural rotation of the joint in question, thereby removing a significant limitation in the movements of the relevant joint.

Specified for this purpose is a device according to the invention with bounding means for limiting the pivoting movement of a hinge to a chosen angular position. Such a device can advantageously have the feature according to the invention that the fastening means comprise at least two divisible rings with adjustable periphery, one of which is connected to the one part and the other to the other part, and the bounding means comprise a flexible, tensively strong element, for instance a strap or cord, of optionally adjustable length, the ends of which are connected to these rings such that the flexible element can bound the pivoting movement of at least one hinge.

It will be apparent that the flexible element has to positioned at a suitable location relative to the hinge in question, and must generally have an at least substantial distance therefrom.

Alternatively, the device can have the feature that the bounding means comprise stop means added to a hinge.

The orthoses known from the two cited publications have a hinge part on either side of the relevant joint. Such orthoses can be referred to as double-sided orthoses. According to the invention the device can advantageously have the feature that said structure is provided on only one side with hinge means. Better cosmetic results are possible with such a device, which is found to be greatly valued by users during tests. Furthermore, with a single-sided orthosis the construction of the multiple hinge according to the invention can be simpler than in the case of a double-sided orthosis.

Two applications of the device according to the invention can be pointed to as important embodiments. In the one embodiment the device has the special feature that the device is a knee orthosis. In the other embodiment the device has the special feature that the device is a knee-ankle-foot orthosis.

BRIEF DESCRIPTION OF THE DRAWINGS

The invention will now be elucidated on the basis of the annexed drawings of several random embodiments, to which the invention is not limited. In the drawings.

DETAILED DESCRIPTION OF THE PREFERRED EMBODIMENTS

Figure 1:
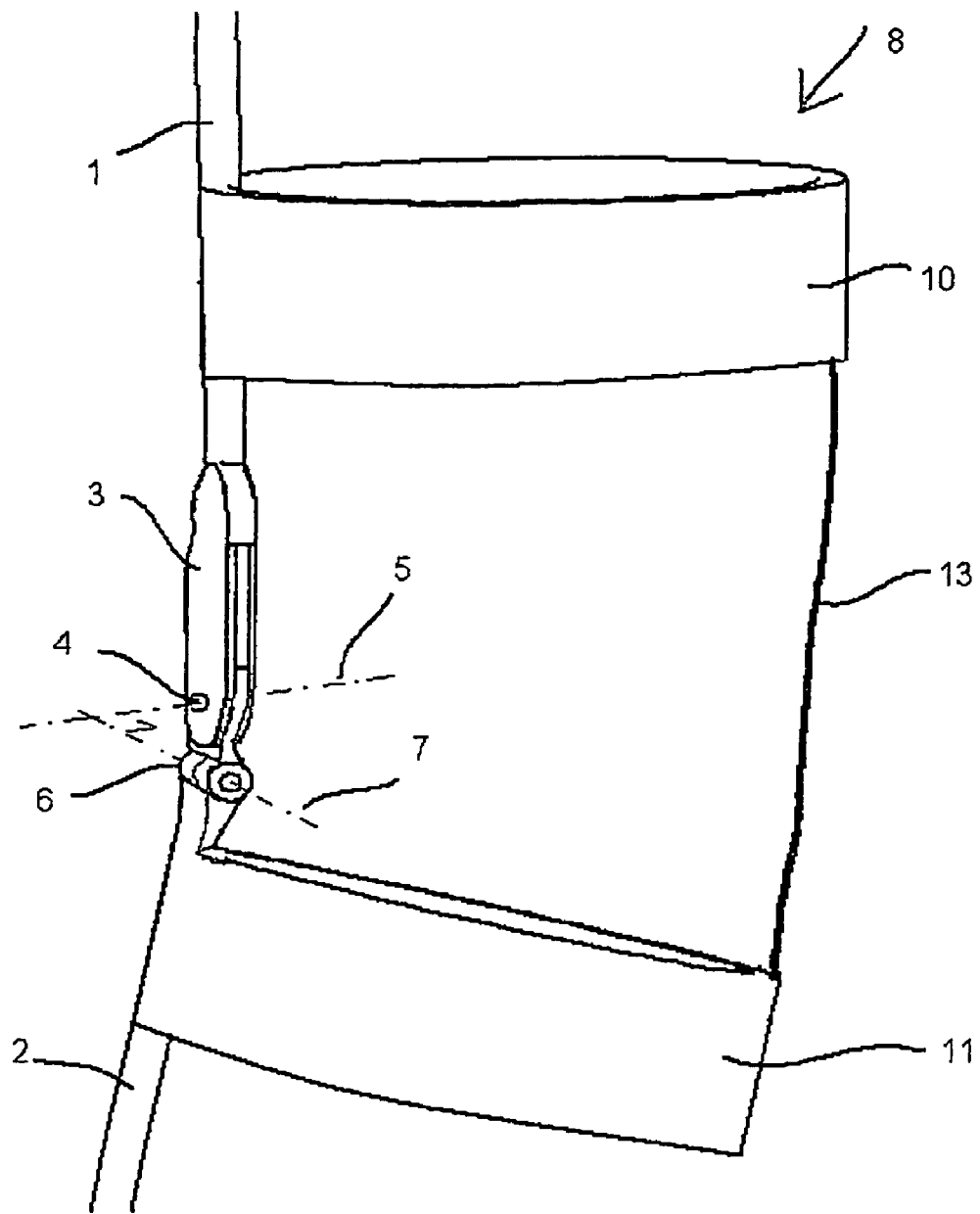
FIG. 1 shows a perspective view of a part of a knee orthosis according to the invention.

Corresponding components are designated in all the figures with the same reference numerals.

FIG. 1 show an orthosis comprising an upper rod 1 and a lower rod 2 which are coupled hingedly to each other by means of hinge means 3. Hinge means 3 comprise an upper hinge 4 with a pivot axis 5 and a lower hinge 6 with a pivot axis 7. The pivot axes 5 and 7 correspond respectively with the usual pivoting movement of the knee and a swivelling movement substantially perpendicular thereto.

Figure 2:
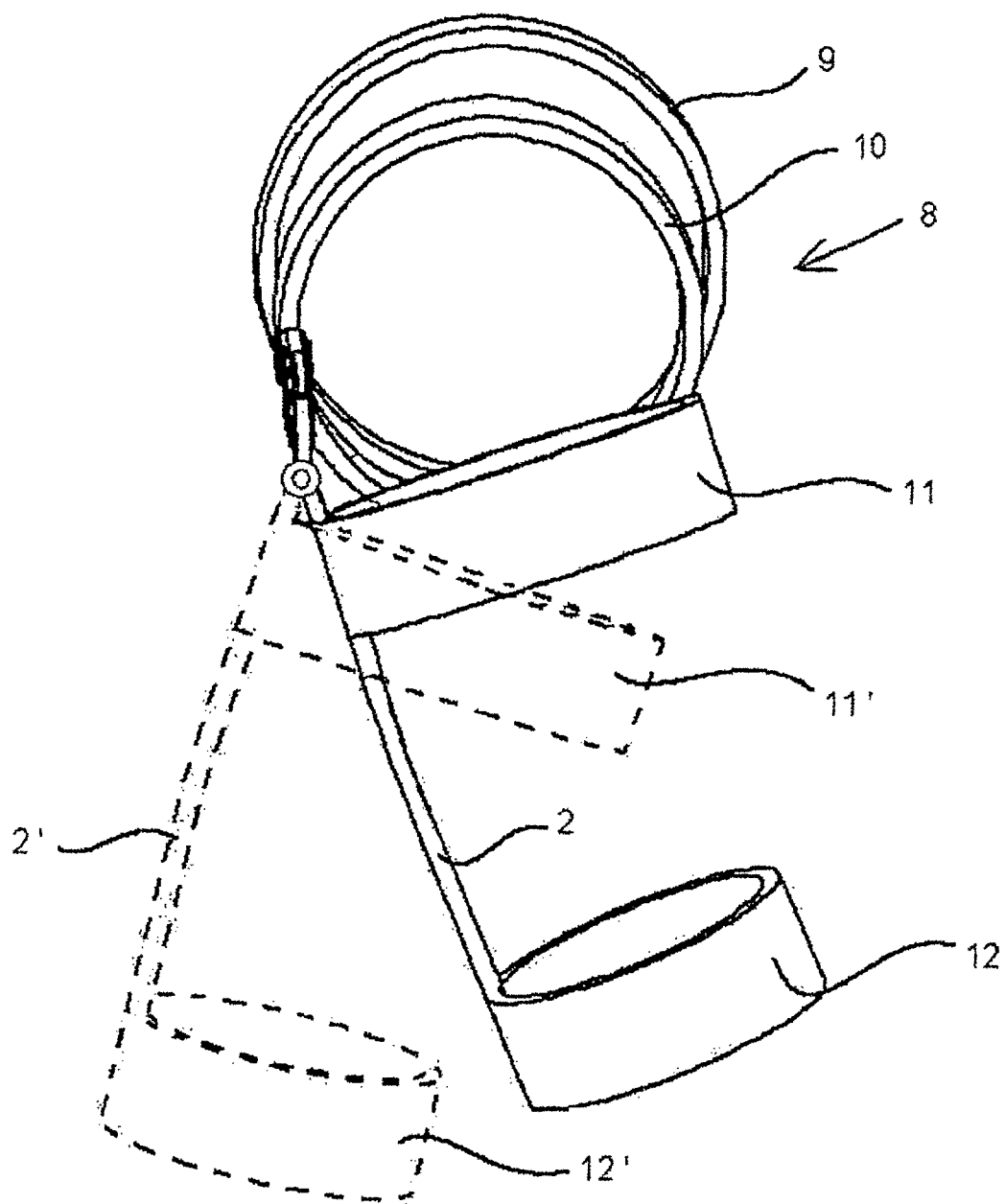
FIG. 2 is a front view of a knee orthosis in which the operation of the additional hinge is shown.
Figure 3:
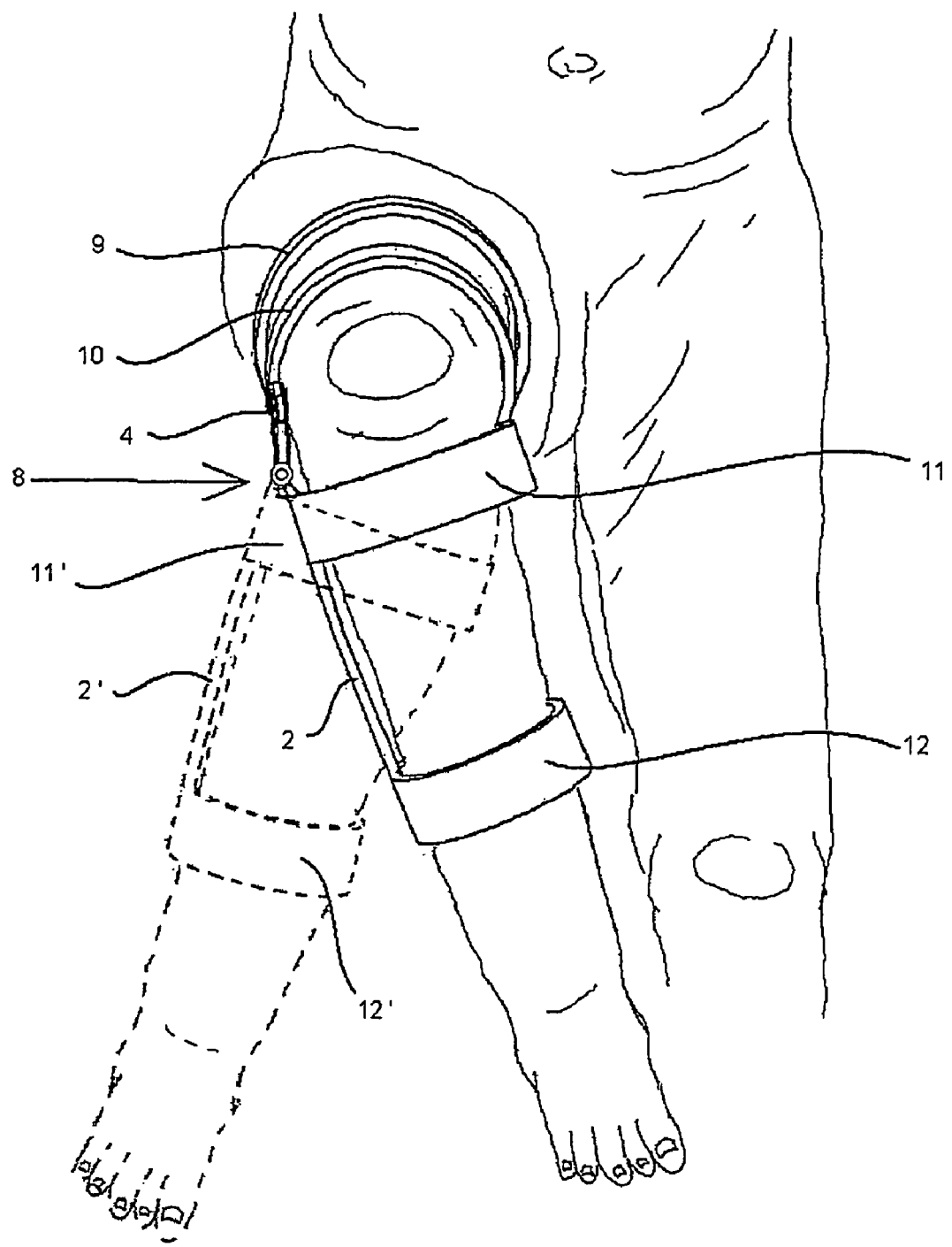
FIG. 3 is a view corresponding with FIG. 2 of the orthosis arranged on a leg.
Figure 4:
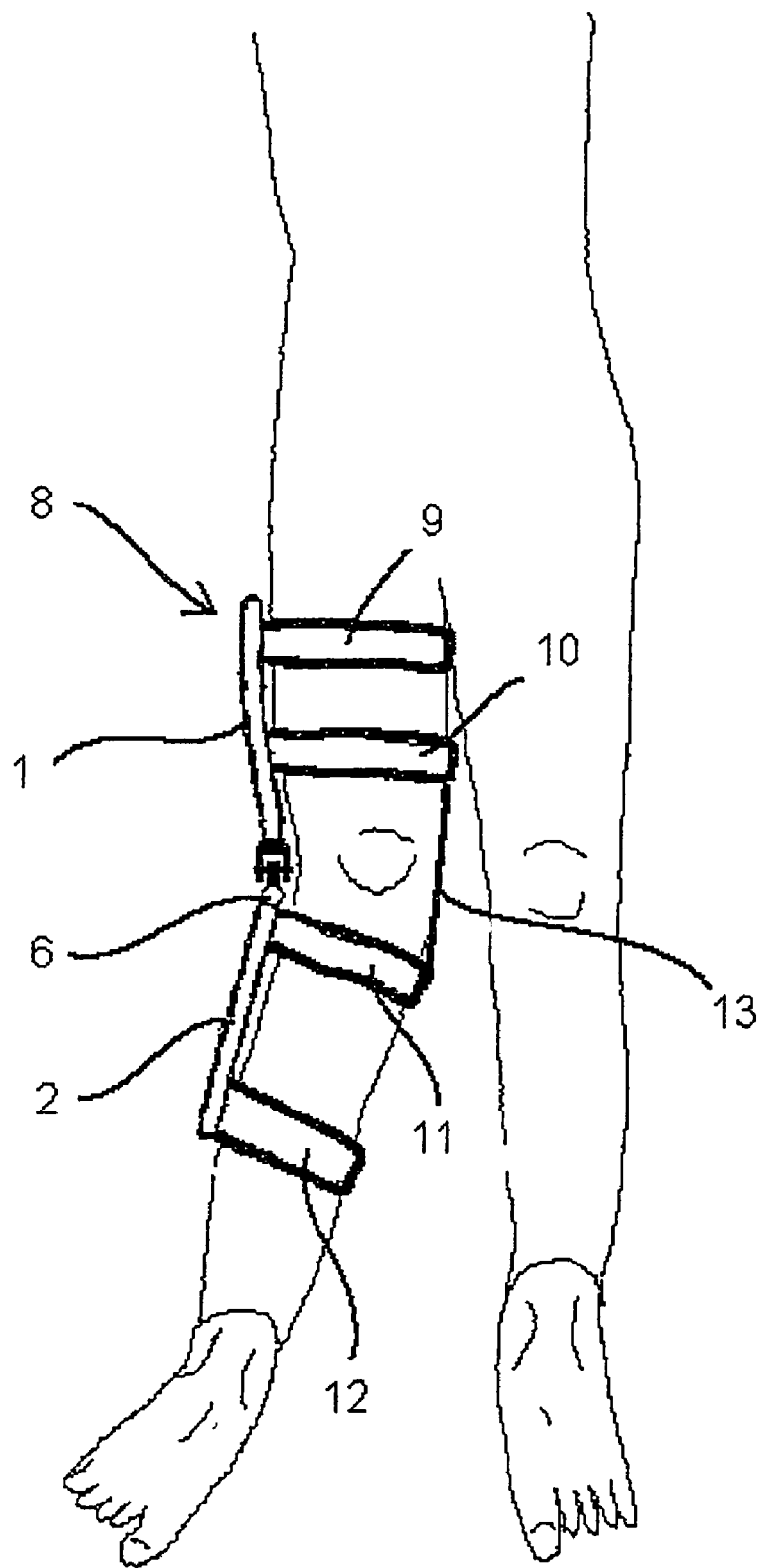
FIG. 4 is a front view of the single-sided orthosis according to FIG. 1, 2, 3 in the situation where the user is also standing on the relevant leg and the bounding means limit lateral displacement to the drawn value.

In order to fasten the orthosis 8 to the leg of a user, use is made of two sets of divisible rings with adjustable periphery, which in accordance with FIGS. 2, 3 and 4 are designated respectively 9, 10, 11, 12.

The rings 10 and 11 are connected to each other by means of a flexible, tensively strong element 13, for instance a strap or cord of optionally adjustable length, such that this element 13 functions as limit to the swivelling movement of hinge 6 and allows the knee to move unhindered over the free swivel zone. Reference is also made in this respect to FIG. 4 in which the flexible element in its tensioned position limits the lateral swivelling movement of said hinge 6. It is noted that it is not necessary in all conditions for the bounding element 13 to be situated diagonally on the other side of rings 10, 11 in relation to hinge 6.

The orthosis 9 can for instance be used to support a knee which may only be loaded in a determined position rotated in the frontal plane, for instance in the case of cartilage problems in the knee.

FIGS. 2 and 3 show the knee orthosis 8 in bent position in accordance with the position of a leg wherein the lower leg makes an angle of for instance about 90 with the upper leg. Particular reference is made in this respect to FIG. 3. said swivelling of the lower leg takes place due to the operation of hinge 4 and a rotation about pivot axis 5. For a lateral displacement of the lower leg, as shown in broken lines, a swivelling takes place about pivot axis 7 of hinge 6. In this manner it is possible to effectively follow the desired movements of the knee, and the functionality of the knee in question can be substantially supported. In FIGS. 2 and 3 in the position drawn in broken lines the relevant components are provided with reference numerals with an accent.

Figure 5:
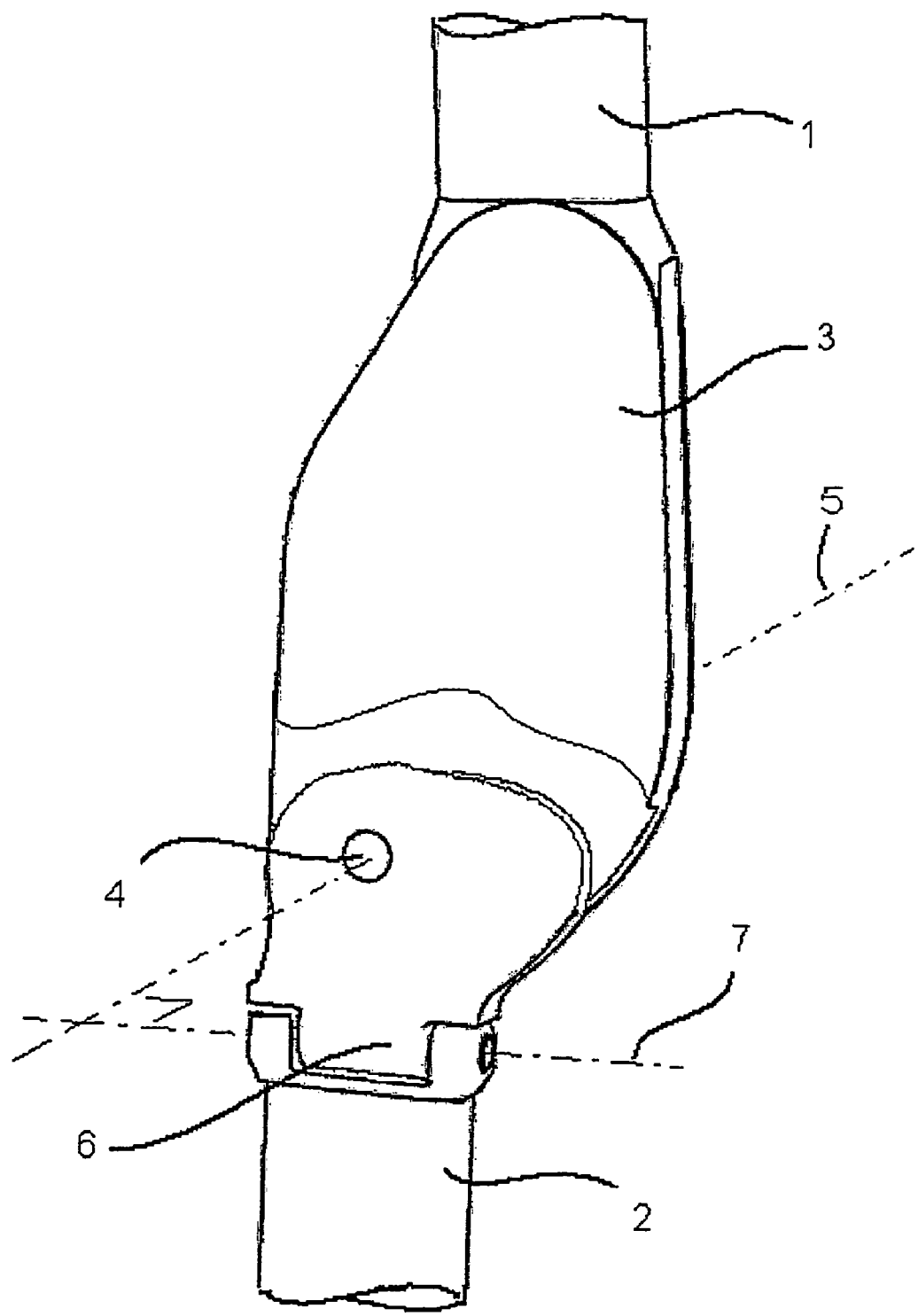
FIG. 5 shows an alternative embodiment of a two-fold hinge.

FIG. 5 shows hinge part 3 with the associated components on enlarged scale.

The invention claimed is:

1. An orthopedic device for supporting the function of at least one part of a human limb with a pivotable joint, on either side of which joint there extends respective limb parts, comprising:

a structure comprising two substantially rigid parts, which parts are coupled to each other by hinge means and each comprise fastening means for temporary fastening to a limb part, wherein the hinge means comprise two hinges and each hinge has a pivot axis and pivots freely about that axis, wherein the respective pivot axes extend in directions which make an angle with each other of 90°±40°, bounding means for limiting at least one of the pivoting movements of at least one of the hinges to unrestrained movement within a chosen range of motion;

wherein the fastening means comprise at least two divisible rings with adjustable periphery, one of which is connected to the one side of the joint and the other to the other side of the joint; and wherein the bounding means comprise a flexible, tensively strong element, the ends of which are connected to the divisible rings such that the flexible element can bound the pivoting movement of at least one hinge.

2. The device as claimed in claim 1, wherein the pivot axes are spaced from one another at a distance, which distance is chosen such that it corresponds with the pivoting characteristics of the relevant joint.

3. The device as claimed in claim 2, wherein the respective pivot axes make an angle with each other of 90°±20°.

4. The device as claimed in claim 1, wherein the bounding means comprise stop means added to a hinge.

5. The device as claimed in claim 1, wherein said structure is provided on only one side with hinge means.

6. The device as claimed in claim 1, wherein the device is a knee orthosis.

7. An orthopedic device for supporting the function of at least one part of a human limb with a pivotable joint on either side of which joint there extends respective limb parts, comprising:

a structure comprising two substantially rigid parts which parts are coupled to each other by hinge means and each comprise fastening means for temporary fastening to a limb part, wherein the hinge means comprise two hinges and each hinge has a pivot axis and pivots freely about that axis, wherein the respective pivot axes extend in directions which make an angle with each other of 90°±40° and, wherein each hinge freely rotates about its respective pivot axis;

bounding means for limiting at least one of the pivoting movements of at least one of the hinges to unrestrained movement within a chosen range of motion;

wherein the fastening means comprise at least two divisible rings with adjustable periphery, one of which is connected to the one side of a joint and the other to the other side of a joint; and wherein the bounding means comprise a flexible, tensively strong element, the ends of which are connected to the divisible rings such that the flexible element can bound the pivoting movement of at least one hinge.

* * * * *